United States Patent [19]
Miyazaki et al.

[11] Patent Number: 5,478,575
[45] Date of Patent: Dec. 26, 1995

[54] POLYMERS HAVING BENZENEBORONIC ACID GROUPS AND INSULIN COMPLEXES OF SAME OF A SUGAR RESPONSE TYPE

[75] Inventors: Tsuyoshi Miyazaki; Yoshishige Murata, both of Tsukuba; Daijiro Shiino; Kazunori Waki, both of Kashiwa; Yasuhisa Sakurai, Tokyo; Teruo Okano, Ichikawa; Kazunori Kataoka, Kashiwa; Yoshiyuki Koyama, Noda; Masayuki Yokoyama, Tokyo; Shigeru Kitano, Kashiwa, all of Japan

[73] Assignee: Nippon Oil & Fats Co., Ltd., Tokyo, Japan

[21] Appl. No.: 37,383

[22] Filed: Mar. 26, 1993

Related U.S. Application Data

[63] Continuation of Ser. No. 599,718, Oct. 19, 1990, abandoned.

[30] Foreign Application Priority Data

Oct. 19, 1989 [JP] Japan ................................. 1-270215
Sep. 13, 1990 [JP] Japan ................................. 2-241191
Sep. 13, 1990 [JP] Japan ................................. 2-241192

[51] Int. Cl.⁶ ............................................. A61K 38/28
[52] U.S. Cl. ........................... 424/487; 424/488; 514/866
[58] Field of Search ............................ 424/488, 487; 514/866

[56] References Cited

FOREIGN PATENT DOCUMENTS 0159521 10/1985 European Pat. Off. .
0284960 5/1988 European Pat. Off. .
8304255 12/1983 WIPO .

OTHER PUBLICATIONS

Makromolekulare Chemie, Macromolecular Chemistry and Physics, vol. 175, No. 3, 1974, pp. 1007–1008.
Chemical Abstracts, vol. 92, No. 22, Jun. 1980, p. 21.
Choi et al. Int. J. of Pharm. 80 (1992) 9–16.
Majestas et al. 189 (1980) 225–231 J. of Chrom.
Journal of Chromatography 189 (1980) 225–231 Majestas et al.
Chem. Abstracts 92:397322 Shiino et al.
Chem. Abstracts 91:312133 Linder et al.
Chem. Abstracts 92:192359.

*Primary Examiner*—Peter F. Kulkosky
*Attorney, Agent, or Firm*—Antonelli, Terry, Stout & Kraus

[57] ABSTRACT

The present invention provides a polymer complex of a sugar response type having boronic acid groups in the polymer. Medicines may be contained or linked, preferably, the medicines have hydroxy groups. The polymer having boronic acid groups and the medicine having hydroxy groups may be linked by boronic acid ester bonds. The complex may also comprises polymers having boronic acid groups and polymers having hydroxy groups, and these polymers may be cross-linked.

5 Claims, 2 Drawing Sheets

POLYMERS HAVING BENZENEBORONIC ACID GROUPS AND INSULIN COMPLEXES OF SAME OF A SUGAR RESPONSE TYPE

This application is a Continuation application of application Ser. No. 599,718, filed Oct. 19, 1990, now abandoned.

BACKGROUND OF THE INVENTION

1. Field of the Invention

The present invention relates to polymer complexes responsive to sugars.

The polymer complexes responsive to sugars can be utilized as a system for treating diabetes mellitus and a sugar sensor by which the release of medicines is controlled in proportion to the concentration of sugars.

2. Description of the Prior Art

Hitherto, it is known that polyvinyl alcohol is gellized by adding boric acid into an aqueous solution of a polyvinylalcohol.

Matrex PBA-30 (Trade mark, manufactured by Amicon Company, benzeneboronic acid-crosslinked agalose gel) is known as a material containing boronic acid groups in the agalose gel. It is used as a gel carrier for an affinity chromatography by using a complex which is formed by the boronic acid groups and sugars containing cis-diol groups in a buffer of pH 8.5.

Generally, in vivo in a healthy condition, homeostasis acts under good conditions. As an example, the ion concentration, the blood glucose value and the like in blood are accurately controlled by high-degree feedback systems to be kept constant. However, if the homeostasis has problems for some reason, for example, when a person contracts a chronic disease such as diabetes or hyperpiesia, regular administration of medicines such as insulin or other drugs is required according as the condition of illness. Then, the dosage and the time should be considered. Change of the homeostasis leading to cause serious consequences must be watched, especially. Hitherto, a main method for treating diabetes is a dietary treatment and self-injection in spite of the progress of medical treatment and flood of medical instruments.

Considering these problems, a system for treating diabetes having an auto-feedback system, by which a medicine is released when it is wanted and the release is stopped in normal conditions, becomes important.

Eliot et al. reported a small-sized portable apparatus which can detect the value of blood glucose by a detector of blood glucose and inject a required amount of insulin into a vein by a pump (J. Am. Med. Assoc.) 241, 223(1979).

Further, S. W. Kim disclosed a system for releasing insulin using a complex of concanavalin A and insulin modified by glucose as a molecular device having glucose sensor function and medicine release function (DIABETES, 32, 499(1983).

In other fields, it becomes important to determine glucose which is a sugar. Glucose sensors are developed in many fields such as medical treatment, food, fermentation and the like.

However, the method for gellizing polyvinyl alcohol by adding boric acid into an aqueous solution of polyvinyl alcohol is not suitable for utilizing in medical treatment because the boric acid added is toxic and the low molecules are easily diffused or permeate into materials.

The self-injection method of insulin has the following disadvantages: 1. the injection amount is different from the necessary amount, 2. the operation is troublesome, 3. there is possibility of troubles such as hypoglycemia coma, and 4. patients must have self control. It is expected to obtain a simple and safe device for controlling insulin release (artificial pancreas).

Moreover, in the method of Eliot et al., since the glucose sensor is connected with the blood stream of a patient through the skin for a long time, there are problems of infection of bacteria passing through the connection or of occurrence of a thrombus. In addition to such problems, safety and reliance of the apparatus are insufficient because there are block of a injection needle caused by crystallized insulin, troubles due to a mechanical or electronic circuit and the like. In addition, since enzyme is used in the conventional glucose sensors, there is a disadvantage of short life, namely about one week.

Further, the system of Kim et al. is prepared by dispensing the complex in a pouch made of a polymer film. When the pouch is embedded intraperitoneally, the glucose concentration increase at the outside of the pouch, an exchange reaction is occurred between insulin modified by glucose which is linked to concanavalin A and glucose, and the insulin is released. On the other hand, when the glucose concentration decreases, the exchange reaction is lowered and the release of insulin is lowered. Namely, the system is an auto-feedback system. However, since concanavalin A having very great toxicity is used in the system, there is a problem of the lack of safety.

As described above, it is desired to obtain a material releasing medicines responsive to glucose concentration which has glucose sensor function and medicine release function in a molecular device. Considering the use for pharmaceuticals, the material should have low toxicity and good formability.

Until now, the utilization of swelling of crosslinking polymer which is changed by complex formation of sugars with boronic acid groups introduced into a synthesized polymer is not reported.

SUMMARY OF THE INVENTION

The object of the present invention is to provide a polymer complex responsive to sugars which has good sugar responsibility, low toxicity and easy processability.

The present invention provides a polymer complex of a sugar response type comprising one or more polymers having boronic acid groups.

Further, the polymer complex of the sugar response type are contained one or more medicines or linked to the medicines. The medicines are released by an exchange reaction, a dissociation, or swelling of the polymer complex responsive to sugar.

Moreover, the polymer used in the present invention is a polymer having boronic acid groups, a copolymer of monomers which can copolymerized with the monomer having boronic acid groups, or a cross-linked polymer. The number-average molecular weights are 10000 to 100000. The cross-linked polymer is obtained by copolymerization of monomers essentially containing a monomer having boronic acid groups and a crosslinking polyfunctional monomer, if necessary, it contains a monomer having hydroxy groups and the other monomers which can copolymerize with these monomers.

Furthermore, the complex of the present invention may comprise one or more polymers having hydroxy groups along with the polymers having boronic acid groups. These polymers may be cross-linked.

Figure 1:
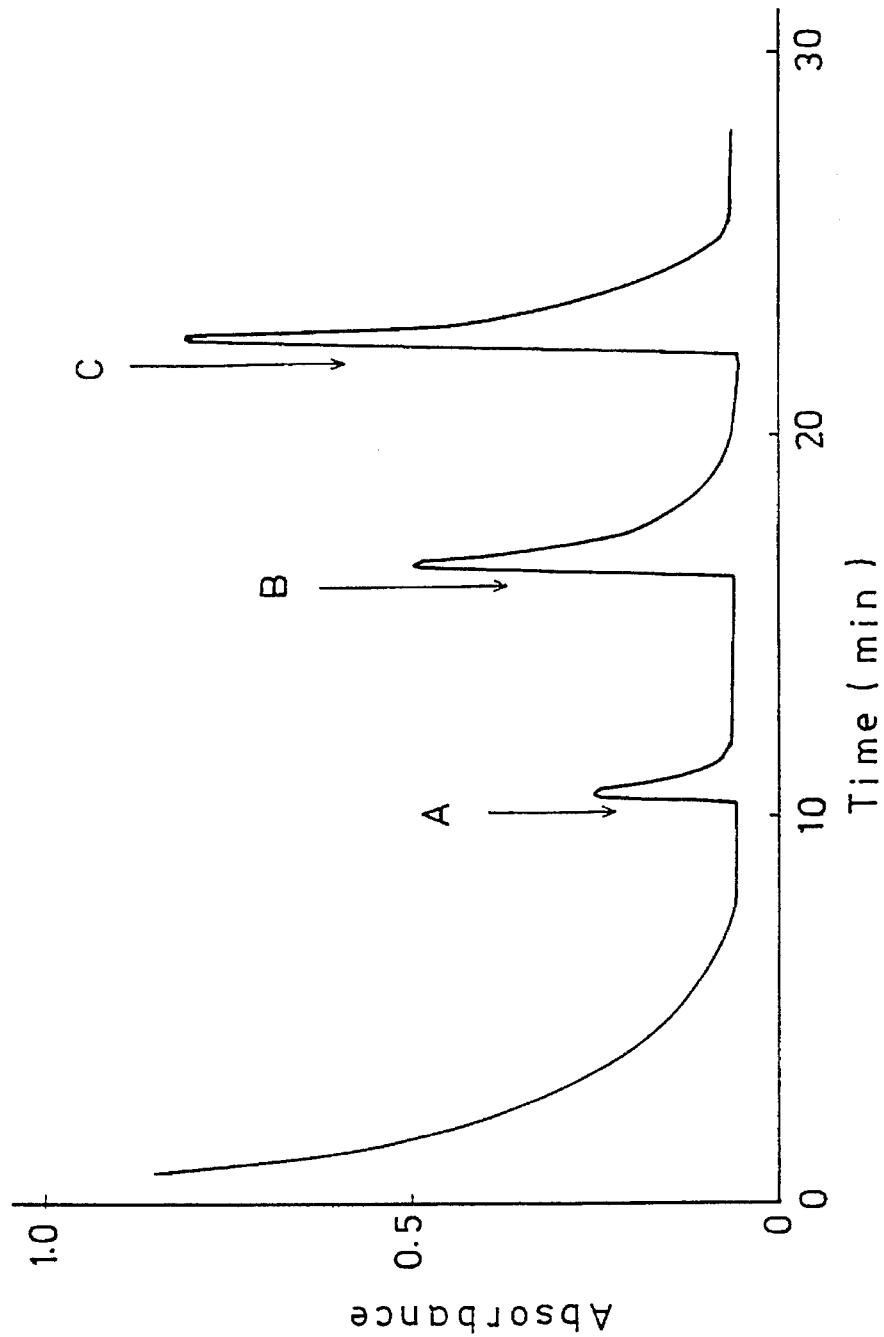
FIG. 1 is a chromatograph obtained in Example 1 as a representative of each example. In the drawing, Arrow head A is a HEPES buffer containing 100 mg/dl of glucose as an effluent, Arrow head B is a HEPES buffer containing 200 mg/dl of glucose as an effluent, and Arrow head C is a HEPES buffer containing 300 mg/dl of glucose as an effluent.

The spindle shows gel strength (cps) and the cross axis shows the time lapsed (minutes), and triangles show 0, black squares show 100, white squares show 200, black circles show 500 and white circles show 1000 mg/dl of sugar concentration, respectively.

DETAILED DESCRIPTION OF THE INVENTION

The monomer having a boronic acid group is, for example, acryloylaminobenzeneboronic acid, methacryloylaminobenzeneboronic acid, 4-vinylbenzeneboronic acid or the like.

The crosslinking polyfunctional monomer is, for example, allyl methacrylate, allyl acrylate, polyethyleneglycol diacrylate, 1,6-hexanediol diacrylate, neopentylglycol diacrylate, tripropyleneglycol diacrylate, polypropyleneglycol diacrylate, 2,2-bis[4-(acryloxydiethoxy)phenyl]propane, 2,2-bis[4-(acryloxypolyethoxy) phenyl]propane, 2-hydroxy-1-acryloxy-3-methacryloxy propane, 2,2-bis[4-(acryloxy-polypropoxy)phenyl] propane, ethyleneglycol dimethacrylate, diethyleneglycol dimethacrylate, triethyleneglycol dimethacrylate, polyethyleneglycol dimethacrylate, 1,3-butyleneglycol dimethacrylate, 1,6-hexanediol dimethacrylate, neopentylglycol dimethacrylate, polypropyleneglycole dimethacrylate, 2-hydroxy-1,3-dimethacryloxy propane, 2,2-bis[4-(methacryloxyethoxy)phenyl] propane, 2,2-bis[4-(methacryloxyethoxydiethoxy)phenyl]propane, 2,2-bis[4-(methacryloxyethoxypolyethoxy)phenyl]propane, trimethylolpropane trimethacrylate, tetramethylolmethane trimethacrylate, trimethylolpropane triacrylate, tetramethylolmethane triacrylate, tetramethylolmethane tetraacrylate, di-pentaerythritol hexaacrylate, N,N'-methylene bisacrylamide, N,N'-methylene bismethacrylamide, diethylene glycol diallyl ether, divinylbenzene or the like.

The monomer copolymerizable with the monomer having a boronic acid group or the polyfunctional monomer which can be used in the present invention is, for example, acrylamide, N-methyl acrylamide, N,N-dimethyl acrylamide, N,N-dimethylaminopropyl acrylamide, N,N-dimethylaminoethyl acrylate and their quaternary salts, and acrylic acid, alkyl acrylates, methacrylic acid, alkyl methacrylates, 2-hydroxyethyl methacrylate, N-vinylpyrrolidone, acryloyl morpholine, acrylonitrile, and styrene and macromonomers.

The usage of the monomer having a boronic acid group is 0.1 to 90 mole % of all monomers, preferably 0.5 to 30 mole %.

The usage of the polyfunctional monomer is 0.01 to 50 mole % of all monomers.

The usage of the copolymerizable monomer is 0.1 to 98 mole % of all monomers.

The methods for producing the polymer complexes of the present invention can be exemplified in the following.

As an example, a monomer having a boronic acid group, a polyfunctional monomer and a monomer copolymerizable with them are copolymerized in one step to obtain a polymer complex of the present invention.

In another example, a monomer having a boronic acid group and a polyfunctional monomer are copolymerized at the first step to obtain a copolymer, and a polyfunctional monomer and a monomer having a polyhydroxy group are impregnated in the copolymer and copolymerized with the copolymer at the second step to obtain a polymer complex of the present invention.

Moreover, a polyfunctional monomer and a monomer having a polyhydroxy group are copolymerized in the first step to obtain a copolymer, and a monomer having a boronic acid group and a polyfunctional monomer are impregnated in the copolymer and copolymerized with the copolymer in the second step to obtain a polymer complex of the present invention.

Further, after crosslinking a polymer having polyfunctional group with a suitable crosslinking agent, a monomer having a boronic acid group and a polyfunctional monomer are impregnated in the cross-linked polymer and copolymerized with the cross-linked polymer to obtain a polymer complex of the present invention.

The cross-linked polymer usable in the present invention is a compound obtained by reacting a polymer having functional groups such as hydroxy groups, amino groups or carboxyl groups with a crosslinking agent such as diisocyanate, dialdehyde, diamine, dicarboxylic acid chloride or the like. The polymer having hydroxy groups is, for example, polyvinyl alcohol, dihydroxy ethylacrylate copolymers, glycerol monomethacrylate copolymers, galactomannan, pullulan, dextran, amylose or the like. The polymer having amino groups is, for example, polyallyl amine, proteins or the like. The polymer having carboxyl groups is, for example, acrylic acid, maleic acid, fumaric acid, itaconic acid or the like.

A cross-linked polymer usable in the present invention is also obtained by a condensation reaction of a polymer, which is a copolymer of a polyfunctional monomer and are unsaturated carboxylic acid, and a compound of a polyhydroxy compound having a primary amino group, for example, tris(hydroxymethyl)amino ethane. Besides, a polymer usable in the present invention is obtained by an amido reaction of amino groups in a polymer or a copolymer of aminostyrene, vinylbenzyl amine or the like, and carboxyl groups in a compound having a polyhydroxy group such as protocatechuic acid, garlic acid, tricine, 2,2-(dihydroxymethyl)propionic acid or the like.

As the polymer having boronic acid groups, the polymer is obtained by amide reaction between a carboxyl group of a polymer or a copolymer of unsaturated carboxylic acids such as acrylic acid, methacrylic acid, itaconic acid, metaconic acid, fumaric acid, maleic anhydride, glycerol monomethacrylate, etc., and an amino group of a boronic acid compound containing an amino group such as m-aminobenzeneboronic acid, in the presence of a condensation agent.

The polymer complex of the present invention can comprise the polymer having boronic acid groups and the polymer having hydroxy groups.

As the polymer having hydroxy groups, a polyvinyl alcohol having a polymerization degree of 100–10000, poly-saccharides such as galactomannan, pullulan, dextran, amylose, etc. can be exemplified. Moreover, a polymers obtained by hydrolyzing a polymeric substance having vinyl acetate groups or a polymer obtained by polymerizing a monomer having hydroxy groups such as monoglycerol methacrylate or by copolymerizing the monomer and the other one or more monomers can be used. The monomer having hydroxy groups is used in the range of 0.1 to 90 mole %.

A polymer obtained by reacting a polymer or a copolymer of unsaturated carboxylic acids such as acrylic acid, methacrylic acid, itaconic acid, metaconic acid, fumaric acid, maleic anhydride, etc. with a compound having hydroxy groups and a primary amino group, for example, tris(hydroxymethyl)amino methane can be used as the polymer having hydroxy groups. Further, a polymer obtained by amido reaction between a polymer having primary amino groups and a compound having a carboxyl group and hydroxy groups can be used. As the polymer having primary amino groups, a polymer obtained by polymerizing or copolymerizing one or more monomers such as aminostyrene, vinylbenzylamine, etc. or proteins can be exemplified. As the compound having a carboxylic group and hydroxy groups, protocatechuic acid, garlic acid, tricine, 2, 2-(dihydroxymethyl)propionic acid, etc. can be exemplified.

In the polymer complex of the present invention, the mixing ratio of the polymer having boronic acid groups and the polymer having hydroxy groups depends on the molecular weight and it is 1:50 to 50:1, preferably 1:10 to 10:1 and more preferably 3:1 to 1:1.

The polymer complex of the present invention is used by mixing a solution of the polymer having boronic acid groups and a solution of the polymer having hydroxy groups. The ratio of the solution of the polymer having boronic acid groups is 0.01 to 50% by weight, preferably 0.1 to 20% by weight. The ratio of the solution of the polymer having many hydroxy groups is 0.01 to 50% by weight, preferably 0.1 to 20% by weight.

The polymers of the present invention are obtained by a common radical polymerization method such as solution polymerization, block polymerization, emulsion polymerization or suspension polymerization at a polymerization temperature of 0° to 100° C. for 10 minutes to 48 hours. One or more compounds selected from the group of benzoyl peroxide, di-isopropyl peroxy dicarbonate, tertiary butyl peroxy-2-ethylhexanoate, tertiary butyl peroxy pivalate, tertiary butyl peroxy di-isobutylate, lauroyl peroxide, azo-bis-isobutyronitrile, 2, 2'-azobis(2, 4-dimethyl valeronitrile and redox initiators can be used in quantities of 0.01 to 5.0% by weight as a polymerization initiator in the reaction.

The polymer complex of the present invention contained medicines or linked to the complex.

All of the medicines which are soluble in water can be used in the complex of the present invention. In particular, insulin, glucagon, somatostatin, adrenal cortical hormone, etc. are effective. The combination of one or more of these medicines also can be used. The polymer complex of the present invention can be used as a sugar sensor along with materials which can be spectro-graphically detected, for example, dyes. In this case, the sugar concentration which can be used is preferably 1 to 10000 mg/dl.

Medicines usable in the above material may be for example, a protein-type medicine modified by sugar chains such as a glucosyl insulin derivative disclosed by the national publication of the translated version No. 59-502065 (1984) of Patent Cooperation Treaty, bronchodillation agents such as isoproterenol, isoetharine, epirine, butanefrine, WG253, trimethoquinol, etc., cordiotonics such as kitoquine and the like, or antituberculotic drugs such as kanamycin, libidomycin, streptomycin, etc. All of them have cis-diol or cis-hydroxy groups in their skeletons. Combination of two or more of these medicines can be used.

Then, the materials containing benzeneboronic acid groups thus obtained and one or more medicines having hydroxy groups described above are reacted in a suitable buffer solution at a temperature of 0°–100° C. for a minute to 24 hours to form boronic acid ester bonds between dihydroxyboronyl groups and hydroxy groups in the skeleton of medicines, and the complex of the present invention is easily obtained. As the buffer solution used in the reaction, a buffer solution of sodium phosphate, sodium acetate. o-chlorophenol, sodium arsenate or sodium carbonate, a Hepes buffer solution or the like can be used. The pH value is preferably 6.0–10.0. Moreover, considering the kind of the medicines employed, a complex of the medicines and the benzeneboronic acid derivative is synthesized, then the complex is reacted by the polymer synthetic or modifying reaction described above, and the complex of the present invention can be prepared. As described above, using the complex of the present invention, materials having many kinds of forms such as inorganic carriers, crosslinking polymers, a natural polymers, hydrogels, water-soluble polymers, fat-soluble polymers can be obtained. Accordingly, the complex of the present invention is applicable to a wide area of medical supplies according to the methods for administrating medicines of injection liquid, tablets, powder or the like in vivo, in vitro or ex vivo.

The complex of the present invention is used in aqueous solvent or in aqueous solution containing 50% or less organic solvent, preferably in buffer solution. Buffer solution containing sodium-phosphate, sodium acetate, o-chlorophenol, sodium arsenate, sodium carbonate, HEPES buffer, CHESS buffer, etc. can be used at pH 6.0 or more, preferably. The complex can be used at a temperature of 1°–50° C.

Sugars to which polymer is responsive are, for example, glucose, galactose, fructose, mannose, etc.

When the complex of the present invention is used in the above aqueous solvent, the sugar concentration is 0.1 mg/dl or more, preferably 1 to 10000 mg/dl.

The complex of the present invention has an auto-feedback system in which, on the one hand, an exchange reaction is occurred between the medicines bonded to benzeneboronic acid and sugar with the increase of glucose concentration in circumstances and the medicines are released, on the other hand, the exchange reaction is lowered with the decrease of glucose concentration and the amount of the medicines released in lowered.

Further, the polymer complex responsive to sugars of the present invention dissociates between the chains of the polymers having boronic groups and the chains of the polymers having hydroxy groups with the increase of sugar concentration. On the other hand, the dissociation between the polymer chains becomes less with the decrease of sugar concentration. Moreover, by using medicines added in the complex wherein the solution of the polymer having boronic acid groups and the solution of the polymer having hydroxy groups are mixed, it becomes a complex for releasing medicines responsive to sugar.

Furthermore, in the complex of the present invention, the cross-linked polymer swells in proportion to the sugar concentration, and when the sugar concentration increases, the materials are allowed to diffuse or penetrate easily. The complex is shrunk by the lowering of the sugar concentration and the diffusion of the materials in the complex is controlled.

Namely, the polymer complex of the present invention can control the release of medicines in response to sugar concentration. The toxicity of the complex is little. It is possible to prepare several forms of the polymer complex. Further, the complex is excellent in good qualities of reliability, safety, etc. and it can be treated easily.

DESCRIPTION OF THE PREFERRED EMBODIMENTS

The following examples illustrate the present invention more specifically, but these will not always be precise in practical applications.

[Polymer complexes of the present invention bonding with medicines]

Firstly, a general method for evaluating the release of medicines responsive to glucose in vitro by using a column is shown in the following.

About 2 ml of a commercially available or private synthesized filler having benzeneboronic acid groups was charged in a propylene column having a diameter of 10 mm and a length of 50 mm and a channel of a gravity-drop type was provided. The effluent was detected with a UV detector (280 nm) having a flow cell. The filler charged in the column was carefully washed by using a HEPES buffer (pH 8.5 or 7.0), and then about 2 ml of a medicine-HEPES buffer of 0.1–1 g/ml was injected to develop, and the contents of the column were incubated at room temperature for 30 minutes. Then, the contents were washed well by using a HEPES buffer (pH 8.5 or 7.0). After confirming that the baseline was steady, the developing solvent was changed with a HEPES buffer containing 300 mg/dl of glucose (manufactured by WAKO JUNYAKU CO., LTD. in Japan, pH 8.5 or 7.0) and the responsibility of medicine release was evaluated.

The result is shown in Table 1.

EXAMPLE 1

HEPES buffer (pH 8.5) as a buffer, Matrex PBA-30 (Trade mark, manufactured by Amicon Company, benzeneboronic acid-crosslinked agalose gel, ligand concentration 30–50 μmol boron/ml gel) as a material containing benzeneboronic acid groups, and glucosyled insulin described in the national publication of the translated version No. 59-502065 of PCT and represented by the following formula as a medicine were used. Insulin was bovine-insulin manufactured by Sigma Company.

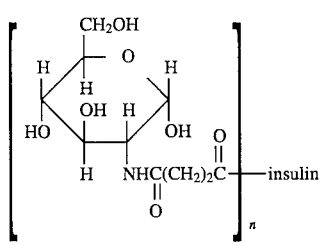

wherein n is a integer of 1–3.

EXAMPLE 2

HEPES buffer (pH 8.5) as a buffer, Matrex PBA-30 (Trade mark, manufactured by Amicon Company, benzeneboronic acid-cross linked agalose gel, ligand concentration 30–50 μmol boron/ml gel) as a material containing benzeneboronic acid groups, and glucosyled insulin described in the national publication of the translated version No. 59-502065 of PCT and represented by the following formula as a medicine were used. Insulin was bovine-insulin manufactured by Sigma Company.

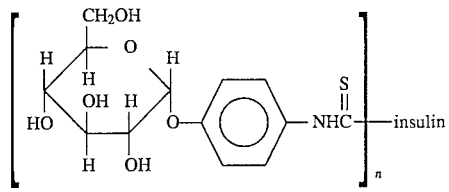

wherein n is a integer of 1–3.

EXAMPLE 3

HEPES buffer (pH 8.5) as a buffer, beaded hydrogel (diameter: about 30 μm) which was prepared by copolymerization of 3-methacryloylaminobenzeneboronic acid/acrylamide/bisacrylamide (5/94.5/0.5 mol/mol/mol) as a material containing benzeneboronic acid groups, and isoproterenol which is a broncho-dilation agent as a medicine were used.

EXAMPLE 4

HEPES buffer (pH 8.5) as a buffer, beaded hydrogel (diameter: about 30 μm) which was prepared by copolymerization of 3-methacryloylaminobenzeneboronic acid/acrylamide/bisacrylamide (5/94.5/0.5 mol/mol/mol) as a material containing benzeneboronic acid groups, and libidomycin which is an antituberculotic drug as a medicine were used.

EXAMPLE 5

HEPES buffer (pH 7.0) as a buffer, silica gel beads (diameter: about 10 μm), which is used for charging in columns, carrying nitrated aminobenzeneboronic acid which was prepared by using the method described in a paper (M. Akashi, Nucleic Acids Symp. Ser., 16, 41(1985)) as a material containing benzeneboronic acid groups, and glucosyled insulin using in Example 1 as a medicine were used.

EXAMPLE 6

HEPES buffer (pH 7.0) as a buffer, silica gel beads (diameter: about 10 μm), which is used for charging in columns, carrying nitrated aminobenzeneboronic acid which was prepared by using the method described in a paper (M. Akashi, Nucleic Acids Syrup. Ser., 16, 41(1985)) as a material containing benzeneboronic acid groups, and glucosyled insulin using in Example 2 as a medicine were used.

EXAMPLE 7

HEPES buffer (pH 8.5) as a buffer, resin (60–120 mesh) which was synthesized by copolymerization of 4-vinylbenzene boronic acid/ethylvinylbenzene/divinylbenzene (95.7/2.0/2.3 mol/mol/mol) as a material containing benzeneboronic acid groups by using a method described in a paper (S. A. Barker, B. M. Hatt, P. J. Somers, R. R. Woodbury, Carbohydrate Research, 26, 55 (1973)), and glucosyled insulin using in Example 2 as a medicine were used.

EXAMPLE 8

HEPES buffer (pH 8.5) as a buffer, beaded hydrogel (diameter: about 300 μm, ligand (boronic acid) concentration: 20–30 μmol/ml polymer, swelling: about 9 g/g polymer) which was synthesized by copolymerization of 3-methacryloylaminobenzeneboronic acid/acrylamide/ethylenbis acrylamide (4/90/6 mol/mol/mol) as a material containing benzeneboronic acid groups, and tris(hydroxymethyl)aminomethane manufactured by Tokyo Kasei Company as a medicine were used.

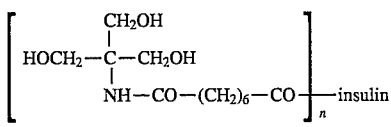

wherein n is a integer of 1–3.

The amounts of medicine release in Examples 1–8 are shown in Table 1.

TABLE 1

| | Amount of Medicine Release (μg/ml) | | | |
|---|---|---|---|---|
| Example | A | B | C | D |
| 1 | 41 | 86 | 151 | 0 |
| 2 | 38 | 82 | 143 | 0 |
| 3 | 5 | 11 | 16 | 0 |
| 4 | 12 | 19 | 24 | 0 |
| 5 | 23 | 49 | 74 | 0 |
| 6 | 21 | 47 | 73 | 0 |
| 7 | 63 | 131 | 196 | 0 |
| 8 | 4 | 8 | 12 | 0 |

As an effluent, HEPES buffer containing glucose of A: mg/dl, B: 200 mg/dl and C: 300 mg/dl was used, respectively. D was HEPES buffer which was not contained glucose. [Polymer complexes of the present invention comprising polymers having hydroxy groups and the polymers having boronic acid groups]

Since the complex formation and dissociation of the polymer chains of boronic acid groups and hydroxy groups was used in the polymer complex of the present invention, the complex formation and the dissociation of the polymer chains should be examined. In the present invention, the viscosity changing with the complex formation was determined. For determination of viscosity changes with the passage of time, the value given with a multi-faculty device (BIOMATIC B-10) for determining blood coagulation times, by which the viscosity changes with blood coagulation is determined, was used. The value obtained with the device was converted into relative viscosity. In explanation of the principle of the device, a feather provided at the tip of an arm is vibrated and the feather is dipped into a solution to be determined. The vibration of the feather is stopped in a viscous solution or gel. Then, the strength of the viscosity is recorded in the value of resistance. The value obtained with the device was converted into viscosity from a calibration curve given with a rotational viscometer.

The turbidity of the solution was determined with a spectrophotometer.

Reference Example 1

Synthesis of a polymer having boronic acid groups

3-Acryloylaminobenzeneboronic acid 0.995 g (5.0 mol %) and N-vinylpyrrolidone 11.0 g (95.0 mol %) in ethanol solvent 109.4 ml with an initiator of 2, 2'-azobis(2,4-dimethyl valeronitrile) 0.298 g (0.01 mol/l) were used. The mixture was polymerized at 45° C. for 0.5 hours in a deaerated and sealed tube. The precipitation of the polymer obtained was repeated three times in ethanol/diethyl ether solvent and the purified polymer was dried. The yield of the polymer thus obtained was 21.7%. From the result of determination of atomic-absorption spectroscopy, it was found that the polymer contained 14.5 mol % of boron. The molecular weight of the polymer obtained was 88000.

The polymer obtained was soluble in ethanol and dimethyl sulfoxide, and insoluble in benzene, n-hexane, acetone, tetrahydrofuran, chloroform, dioxane, diethyl ether, etc. It was little soluble in distilled water. It was easily soluble in an alkali solution. The polymer obtained was dissolved in an aqueous solution of 0.05N sodium hydroxide. The solution was titrated with an aqueous solution of 0.1N hydrochloric acid to obtain a pH value when a turbidity appeared. As a result, the turbidity appeared at pH 9.

Reference Example 2

Synthesis of a polymer having boronic acid groups

The same procedure as in Reference example 1 was repeated except that the composition ratios were changed to 2.5 mole % of 3-acryloylaminobenzeneboronic acid and 97.5 mole % of N-vinylpyrrolidone.

The yield of the polymer obtained was 19.2%. The polymer contained 12.0 mole % of boron by the measurement of atomic spectroscopy. The molecular weight was 80000.

Reference Example 3

Synthesis of a polymer having boronic acid groups

The same procedure as in Reference example 1 was repeated except that the composition ratios were changed to 1.0 mole % of 3-acryloylaminobenzeneboronic acid and 99.0 mole % of N-vinylpyrrolidone.

The yield of the polymer obtained was 17.5%. The polymer contained 9.8 mole % of boron by the measurement of atomic spectroscopy. The molecular weight was 80000.

Reference Example 4

Synthesis of a polymer having boronic acid groups

3-Acryloylaminobenzeneboronic acid 0.386 g (2.5 mol %) and acrylamide 5.612 g (97.5 mole %) in 114 ml of distilled water/ethanol (v/v=3/1) with an initiator of ammonium persulfate (0.025 mol/l) were polymerized in a degassed sealed tube at 45° C. for 45 minutes. The polymer obtained was precipitated from water/methanol solvent three times. The polymer purified was dried. The yield was 70%. The molecular weight was 70000.

EXAMPLE 9

The polymer obtained in Reference example 1 as a polymer containing boronic acid groups and a polyvinyl alcohol having a molecular weight of 88000 as a polymer containing hydroxy groups (saponification rate: 99.5%) were used in a mixture ratio of 1:1 by changing the polymer solution concentration as shown in Table 2. The mixture was reacted to obtain a complex. The viscosity was determined. The results are shown in Table 2.

EXAMPLE 10

The polymer obtained in Reference example 1 as a polymer containing boronic acid groups and a polysaccharide (galactose) as a polymer containing hydroxy groups (saponification rate: 99.5%) were used in a mixture ratio of 1:1 by changing the polymer solution concentration as shown in Table 2. The mixture was reacted to obtain a complex. The viscosity was determined. The results are shown in Table 2.

COMPARATIVE EXAMPLE 1

A polymer, which was obtained in the same procedure as in Reference example 1 repeated except that 3-acryloylaminobenzeneboronic acid was not added, was used along with a polyvinyl alcohol having a molecular weight of 88000 as a polymer containing hydroxy groups (saponification rate: 99.5%) in a mixture ratio of 1:1 by changing the polymer solution concentration as shown in Table 2. The mixture was reacted to obtain a complex. The viscosity was determined. The results are shown in Table 2.

TABLE 2

|  | Polymer concentration (%) | | Viscosity (cps) |
| --- | --- | --- | --- |
|  | Polymer containing boronic acid groups | Polymer containing hydroxy groups |  |
| Example 9 | 0.25 | 0.25 | 1.0 |
|  | 0.50 | 0.50 | 17.8 |
|  | 0.75 | 0.75 | 45.6 |
|  | 1.00 | 1.00 | 59.8 |
| Example 10 | 0.25 | 0.25 | 1.0 |
|  | 0.50 | 0.50 | 18.2 |
|  | 0.75 | 0.75 | 46.1 |
|  | 1.00 | 1.00 | 62.5 |
| Comparative Example 1 | 0.25* | 0.25 | 1.0 |
|  | 0.50* | 0.50 | 1.0 |
|  | 0.75* | 0.75 | 1.0 |
|  | 1.00* | 1.00 | 1.0 |

*Polymer having none of boronic acid groups.

In Table 2, while the viscosity of the complexes obtained with a polymer having none of boronic acid groups is constant and about 1.0 (cps), the viscosity of the complexes obtained with a polymer having boronic acid groups apparently increases with the rise of polymer concentration.

EXAMPLE 11

The polymer obtained in Reference example 1 as a polymer containing boronic acid groups and a polyvinyl alcohol having a molecular weight of 25500 as a polymer containing hydroxy groups (saponification rate: 99.6%) were used at the polymer solution concentration of 0.5%. Changing a mixture ratio, the mixture was reacted to obtain a complex. The viscosity was determined. The results are shown in Table 3.

EXAMPLE 12

A complex was obtained in the same procedure as in Example 11 by changing the polymer solution concentration to 0.75%. The viscosity was determined. The results are shown in Table 3.

EXAMPLE 13

A complex was obtained in the same procedure as in Example 11 by changing the polymer solution concentration to 1.0%. The viscosity was determined. The results are shown in Table 3.

EXAMPLE 14

The polymer obtained in Reference example 2 as a polymer containing boronic acid groups and a polyvinyl alcohol having a molecular weight of 25500 as a polymer containing hydroxy groups (saponification rate: 99.6%) were used by changing the mixing ratio at the polymer solution concentration of 1.0%. The mixture was reacted to obtain a complex. The viscosity changes were determined. The results are shown in Table 3.

In Table 3, the results of Example 11 to 14 are shown. The viscosity changes of complexes synthesized by changing the polymer concentration and the mixing ratio of polymers having boronic acid groups and polymers having hydroxy groups are shown in the table.

TABLE 3

|  | Polymer Concentration (%) | | Mixing ratio (by weight) | | Viscosity (cps) |
| --- | --- | --- | --- | --- | --- |
|  | B | T | B | T |  |
| Example 11 | 0.5 | 0.5 | 7 | 1 | 1.0 |
|  |  |  | 3 | 1 | 1.5 |
|  |  |  | 1.7 | 1 | 1.8 |
|  |  |  | 1 | 1 | 1.9 |
|  |  |  | 1 | 1.7 | 1.0 |
|  |  |  | 1 | 3 | 1.0 |
| Example 12 | 0.7 | 0.7 | 7 | 1 | 3.0 |
|  |  |  | 3 | 1 | 13.8 |
|  |  |  | 1.7 | 1 | 14.7 |
|  |  |  | 1 | 1 | 10.2 |
|  |  |  | 1 | 1.7 | 2.7 |
|  |  |  | 1 | 3 | 2.4 |
| Example 13 | 1.0 | 1.0 | 7 | 1 | 15.2 |
|  |  |  | 3 | 1 | 22.2 |
|  |  |  | 1.7 | 1 | 24.8 |
|  |  |  | 1 | 1 | 23.5 |
|  |  |  | 1 | 1.7 | 15.2 |
|  |  |  | 1 | 3 | 7.1 |
| Example 14 | 1.0 | 1.0 | 7 | 1 | 4.7 |
|  |  |  | 3 | 1 | 15.7 |
|  |  |  | 1.7 | 1 | 13.5 |
|  |  |  | 1 | 1 | 12.3 |
|  |  |  | 1 | 1.7 | 4.1 |
|  |  |  | 1 | 3 | 2.6 |

B: Polymer having boronic acid groups
T: Polymer having hydroxy groups

From the result, the formation of complexes is apparently found in the ratios of 3:1 to 1:1 of the polymers having boronic acid groups and the polymers having hydroxy groups.

EXAMPLE 15

Figure 2:
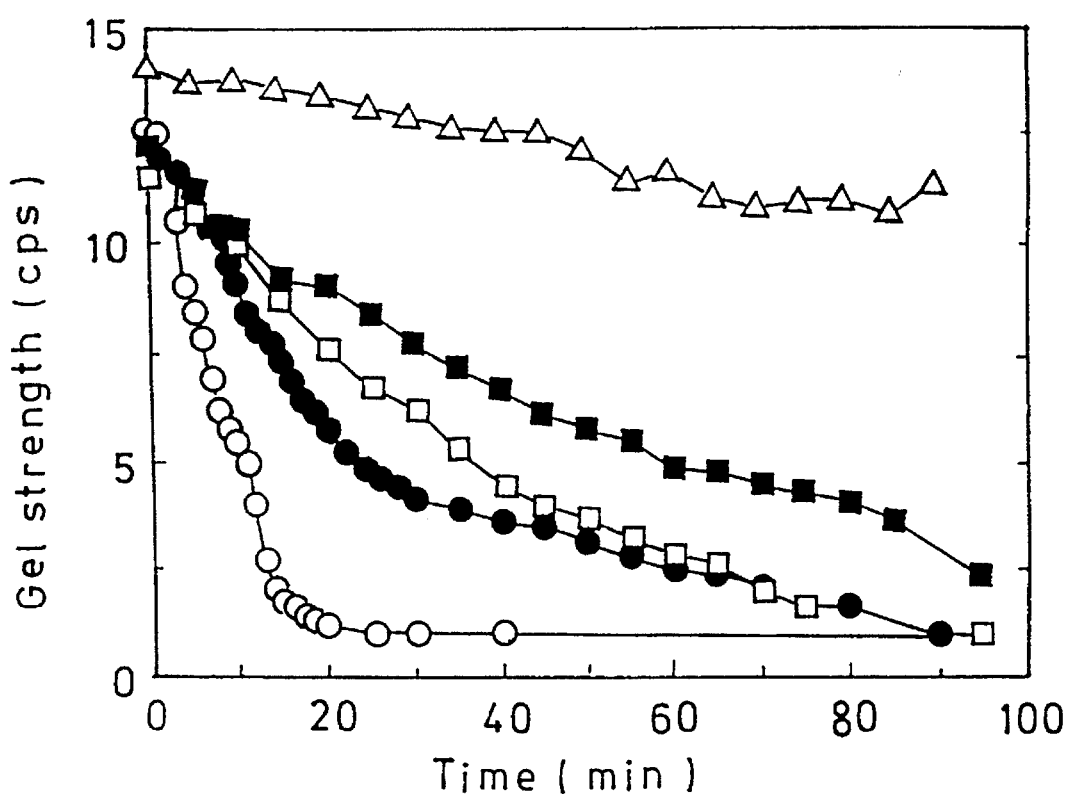
FIG. 2 is a graph which shows viscosity changes lowering with dissociation of the complex obtained in Example 15, in case of the addition of glucose having each sugar concentration with the elapse of time.

A 0.75% aqueous solution of the polymer having boronic acid groups obtained in Reference example 1 and a 0.75% aqueous solution of a polyvinyl alcohol (saponification rate: 99.6%) were mixed in a mixture ratio of 1:1 to form a complex. Then, glucose having a sugar concentration of 0, 100, 200, 500, and 1000 mg/dl was added to the complex, respectively. The changes of viscosity lowering with the dissociation of the complex were examined with the elapse of time. The results are shown in FIG. 2.

In the figure, a sugar concentration of 0, 100, 200, 500 and 1000 mg/dl is triangles, black squares, white squares, black circles and white circles, respectively.

As shown in the figure, it is found that the viscosity lowering with the dissociation of the complex becomes rapid with the increase of the sugar concentration. Particularly, in the case of the sugar concentration of 1000 mg/dl, the viscosity becomes constant 20 minutes after.

EXAMPLE 16

A complex was synthesized with a 2% solution of the polymer obtained in Reference 4 as a polymer having boronic acid groups, a polyvinyl alcohol having a molecular weight of 88000 as a polymer having hydroxy groups and insulin. The complex obtained was put in a dialysis membrane and the insulin release was examined in a phosphoric acid buffer (pH=7.4) in the absence of glucose and in the presence of glucose of 1000 mg/dl, respectively. The insulin used was bovine insulin manufactured by Sigma Company. The insulin was determined by UV measurement (274 nm). The dialysis membrane used was Spectra/Pore 7 (differential molecular weight 25000), a dialysis tube manufactured by Spectra Company. The insulin concentration in the complex was 0.5 mg/ml. 6 ml of the complex charged in the dialysis tube was put in 12 ml of the buffer or the buffer containing glucose to determine the concentration of the insulin released. The concentration of the insulin released three hours after was 11 µg/ml in the case of the buffer alone and 36 µg/ml in the case of the buffer containing 1000 mg/dl of glucose, respectively.

[Polymer complexes of the present invention comprising cross-linked polymers as polymers having boronic acid groups]

EXAMPLE 17

To 3-methacryloylaminobenzeneboronic acid 2.05 g (10 mmol) and 2-hydroxyethyl methacrylate 11.7 g (90 mmol), a crosslinking agent of ethylene glycol dimethacrylate 0.099 g (0.5 mmol) and an initiator of tertiary butyl peroxy-2-ethyl hexanoate 0.07 g were added. After the atmosphere was replaced with nitrogen, the mixture was poured into a vessel for preparing membrane.

A membrane was obtained by the following process. Polyethylene terephthalate film having a thickness of 100 µm was applied on two glass plates. A frame, (Teflon, thickness: 0.1–1.0 mm) for pouring a monomer solution between the glass plates was made. After pouring the monomer solution, the frame was put between the glass plates. The glass plates were put into an oven. The solution was polymerized at 60° C. for 12 hours in a stream of nitrogen. After the complex obtained was immersed in distilled water or buffer, it was examined by UV (254 nm) measurement whether benzene boronic acid groups of the complex were released or not. Although the complex was immersed for ten days, the release was not observed.

The swelling change of the complex was examined in a buffer solution at 37° C. in the presence of sugar and in the absence of sugar. The results are shown in Table 4.

EXAMPLE 18

To 3-methacryloylaminobenzeneboronic acid 2.05 g (10 mmol), 2-hydroxyethyl methacrylate 10.4 g (80 mmol) and diethylaminoethyl methacrylate 1.85 g (10 mmol), a crosslinking agent of ethyleneglycol dimethacrylate 0.099 g (0.5 mmol) and an initiator of tertiary butyl peroxy-2ethyl hexanoate 0.072 g were added. After the atmosphere was replaced with nitrogen for 20 minutes, the mixture was poured into a vessel for preparing membrane.

A membrane was obtained by the same process as described in Example 17. The release of benzene boronic acid groups from the complex obtained was examined by the same method as used in Example 17. Although the complex was immersed in distilled water and buffer for ten days, the release was not observed.

The swelling change of the complex obtained was examined in a buffer solution at 37° C. in the presence of sugar and in the absence of sugar. The results are shown in Table 4.

EXAMPLE 19

To 3-methacryloylaminobenzeneboronic acid 0.82 g (4 mmol) and N, N-dimethylacrylamide 3.569 g (36 mmol) in dimethylformamide 14.335 g, a crosslinking agent of ethyleneglycol dimethacrylate 0.396 g (2 mmol) and an initiator of tertiary butyl peroxy-2-ethyl hexanoate 0.096 g were added. After the atmosphere was replaced with nitrogen for 20 minutes, the mixture was poured into a vessel for preparing membrane.

A membrane was obtained by the same process as described in Example 17. The release of benzene boronic acid groups from the complex obtained was examined by the same method as used in Example 17. Although the complex was immersed in distilled water and buffer for ten days, the release was not observed.

The swelling change of the complex obtained was examined in a buffer solution at 37° C. in the presence of sugar and in the absence of sugar. The results are shown in Table 4.

EXAMPLE 20

To dimethylformamide 14.085 g, 3-methacryloylaminobenzeneboronic acid 0.41 g (2 mmol), N, N-dimethylacrylamide 3.569 g (36 mmol) and glycerol monomethacrylate 0.32 g (2 mmol) were added. To the mixture, a crosslinking agent of ethylene glycol dimethacrylate 0.396 g (2 mmol) and an initiator of tertiary butyl peroxy-2-ethyl hexanoate 0.094 g were added. After the atmosphere was replaced with nitrogen for 20 minutes, the mixture was poured into a vessel for preparing membrane.

A membrane was obtained by the same process as described in Example 17. The release of benzene boronic acid groups from the complex obtained was examined by the same method as used in Example 17. Although the complex was immersed in distilled water and buffer for ten days, the release was not observed.

The swelling change of the complex obtained was examined in a buffer solution at 37° C. in the presence of sugar and in the absence of sugar. The results are shown in Table 4.

EXAMPLE 21

The same procedure as in Example 20 was repeated except that the monomer of 3-methacryloylaminobenzeneboronic acid was changed to 3-acryloylaminobenzeneboronic acid 0.764 g (4 mmol). The release of benzene boronic acid groups from the complex obtained was examined by the same method as used in Example 17. Although the complex was immersed in distilled water and buffer for ten days, the release was not observed.

The swelling change of the complex obtained was examined in a buffer solution at 37° C. in the presence of sugar and in the absence of sugar. The results are shown in Table 4.

EXAMPLE 22

In the first step, 20 ml of a 5 wt % aqueous solution of polyvinyl alcohol having a polymerization degree of 500, 0.95 ml of 2.5% aqueous solution of glutaraldehyde and 1.0 ml of a 10% aqueous solution of sulfuric acid were put in a plate and permitted to stand for 24 hours. The polymer cross-linked was put in distilled water and washed three times to remove unreactive materials. In the second step, 3-methacryloylaminobenzeneboronic acid 0.41 g (21 mmol), N, N-dimethylacrylamide 9.72 g (98 mmol), N, N'-methylene-bisacrylamide 0.385 g (2.5 mmol) and 95 ml of distilled water were added to the polymer obtained. The mixture was immersed in an aqueous solution containing an initiator of ammonium persulfate 0.5 g for 48 hours. After the atmosphere was replaced with nitrogen for 2 to 3 hours, the mixture was polymerized in an oven at a temperature of 80° C. for 12 hours in a stream of nitrogen.

The complex obtained was put in distilled water and washed three times to remove unreactive materials. The release of boronic acid groups from the complex was examined by the same method as used in Example 17. Although the complex was immersed in distilled water and a buffer solution for ten days, the release was not observed.

The swelling change of the complex was examined in a buffer solution at 37° C. in the presence of sugar and in the absence of sugar. The results are shown in Table 4.

EXAMPLE 23

In the first step, 20 ml of a 5 wt % dimethyl sulfoxide solution of polyvinyl alcohol having a polymerization degree of 500 and 0.2 g of an triisocyanate of KORONATE HL manufactured by Nippon Polyurethane Industrial Co. Ltd. were put in a plate and crosslinked in an oven at a temperature of 80° C. for 72 hours. The polymer crosslinked was put in dimethyl sulfoxide and washed three times to remove unreactive materials. In the second step, the polymer was immersed in a solution containing 3-methacryloylaminobenzeneboronic acid 1.025 g (5 mmol), N, N-dimethylacrylamide 9.418 g (95 mmol), ethyleneglycol dimethacrylate 0.495 g (2.5 mmol), 98.4 ml of dimethyl sulfoxide and an initiator of tertiary butyl peroxy-2-ethylhexanoate 0.55 g for 48 hours. After the atmosphere was replaced with nitrogen for 2 to 3 hours, the mixture was polymerized in an oven at a temperature of 60° C. for 12 hours in a stream of nitrogen.

The complex obtained was put in dimethyl sulfoxide and washed three times to remove unreactive materials. The dimethyl sulfoxide in the complex is gradually replaced with distilled water. The release of boronic acid groups from the complex was examined by the same method as used in Example 17. Although the complex was immersed in distilled water and a buffer solution for ten days, the release was not observed.

The swelling change of the complex was examined in a buffer solution at 37° C. in the presence of sugar and in the absence of sugar. The results are shown in Table 4.

EXAMPLE 24

To 12 ml of distilled water, 3-methacryloylaminobenzeneboronic acid 33 mg (0.16 mmol), acrylamide 1.14 g (16.0 mmol) and glycerol monomethacrylate 26 mg (0.16 mmol) were added. To the mixture, a crosslinking agent of N, N'-methylene-bisacrylamide 90 mg (0.58 mmol) and 0.2 ml of an aqueous solution of ammonium persulfate (0.6 g/ml) as an initiator and 0.1 ml of N, N, N', N'-tetramethylethylenediamine were added. Then, the mixture was added to a solution containing a solvent of toluene-chloroform and 0.4 ml of ARCER C (manufactured by Kanto Kasei Company) to obtain a complex by reversed phase suspension polymerization at 0° C. for 1 hour in a stream of nitrogen. The release of benzene boronic acid groups from the complex obtained was examined by the same method as used in Example 17. Although the complex was immersed in distilled water and buffer for ten days, the release was not observed.

The swelling change of the complex obtained was examined in a buffer solution at 37° C. in the presence of sugar and in the absence of sugar. The results are shown in Table 4.

COMPARATIVE EXAMPLE 2

To 2-hydroxyethyl methacrylate 13.0 g (100 mmol), a crosslinking agent of ethyleneglycol dimethacrylate 0.099 g (0.5 mmol) was added. The mixture was polymerized by the same method as shown in Example 17.

The swelling change of the complex obtained was examined in a buffer solution at 37° C. in the presence of sugar and in the absence of sugar. The results are shown in Table 4.

COMPARATIVE EXAMPLE 3

The same procedure as in Example 19 was repeated except that the amount of N, N-dimethylacrylamide was changed to 3.965 g (40 mmol) and the amount of dimethylformamide was changed to 13.084 g without addition of 3-methacryloylaminobenzeneboronic acid.

The swelling change of the complex obtained was examined in a buffer solution at 37° C. in the presence of sugar and in the absence of sugar. The results are shown in Table 4.

COMPARATIVE EXAMPLE 4

The same procedure as in Example 19 was repeated except that 3-methacryloylaminobenzeneboronic acid was changed to glycerol monomethacrylate 0.64 g (4 mmol).

The swelling change of the complex obtained was examined in a buffer solution at 37° C. in the presence of sugar and in the absence of sugar. The results are shown in Table 4.

The swelling degrees of the complexes obtained in Examples 17 to 24 and Comparative examples 2 to 4 are shown in Table 4.

The swelling degree is represented as an amount (g) of solvent contained in 1 g of the complex.

The solution used in the measurement are

A: physiologic phosphoric acid buffer (pH=7.4),
B: HEPES buffer (pH=8.5),
C: HEPES buffer (pH=8.5), glucose 100 mg/dl,
D: HEPES buffer (pH=8.5), glucose 1000 mg/dl and
E: HEPES buffer (pH=8.5), galactose 1000 mg/dl.

TABLE 4

| | Swelling Degree | | | | |
|---|---|---|---|---|---|
| | A | B | C | D | E |
| Example | | | | | |
| 17 | 0.40 | 0.43 | 0.49 | 0.69 | 0.78 |
| 18 | 0.41 | 0.43 | 0.47 | 0.67 | 0.75 |
| 19 | 4.47 | 4.58 | 5.18 | 7.27 | 8.24 |
| 20 | 6.87 | 7.30 | 7.54 | 8.25 | 8.61 |
| 21 | 6.90 | 7.59 | 7.88 | 8.51 | 8.89 |
| 22 | 10.1 | 10.5 | 10.7 | 11.0 | 11.1 |
| 23 | 12.2 | 12.8 | 13.2 | 14.0 | 14.2 |
| 24 | 9.38 | 9.52 | 9.60 | 9.82 | 9.88 |

TABLE 4-continued

| | Swelling Degree | | | | |
|---|---|---|---|---|---|
| | A | B | C | D | E |
| Comparative example | | | | | |
| 2 | 0.40 | 0.41 | 0.41 | 0.41 | 0.41 |
| 3 | 6.91 | 6.93 | 6.92 | 6.94 | 6.94 |
| 4 | 6.53 | 6.54 | 6.53 | 6.54 | 6.54 |

As shown in Table 4, the swelling degrees of the complexes obtained in Examples are increased in response to the sugar concentration. On the other hand, the swelling degrees of the complexes obtained in Comparative examples are constant.

EXAMPLE 25

In the complex of Example 19, the permeating of insulin is examined in a constant temperature bath at 37° C. by using a permeation equipment separated into two layers (20 ml/layer) with membrane (a diameter of 20 mm). HEPES buffer (pH=8.5) containing 0.5 mg/ml of insulin was put in one layer of the equipment and HEPES buffer or HEPES buffer containing 1000 mg/dl of glucose was put in the other layer. By using bovine insulin manufactured by Sigma Company, insulin was determined with UV (274 nm).

As a result, the insulin concentration of the layer to which insulin permeated six hours after was 32 µg/ml in case of HEPES buffer alone and 63 µg/ml in case of HEPES buffer containing 1000 mg/dl of glucose, respectively.

We claim:

1. A method for treating diabetes comprising, administering a polymer insulin complex to a diabetic patient wherein insulin is released from said complex in response to a sugar concentration in blood of the diabetic patient, wherein the polymer insulin complex contains at least one polymer having benzene boronic acid groups and insulin or an insulin derivative having hydroxy groups;

said polymer having a molecular weight between 5,000 and 300,000, the content of benzene boronic acid monomers forming said polymer having boronic acid groups being 0.1 to 30 mole % and the at least one polymer being a homopolymer or copolymer of 3-acryloylaminobenzeneboronic acid, 3-methacryloylaminobenzenebornonic acid or 4-vinybenzeneboronic acid, and wherein said polymer insulin complex releases 0 to 500 micrograms per milliliter of said insulin or said insulin derivative having hydroxy group in response to 0 to 500 milligrams per deciliter of sugar in the blood of said diabetic patient such that an increase in blood sugar causes an increase in said insulin or said insulin derivative being released from said polymer insulin complex.

2. A polymer insulin complex of a sugar response type for delivery of insulin or its derivative to blood in the treatment of diabetes comprising at least one polymer having benzene boronic acid groups and insulin or an insulin derivative having hydroxy groups; the molecular weight being 5000–300,000, the content of benzene boronic acid monomers forming the at least one polymer having benzene boronic acid groups being 0.1 to 30 mole % and said at least one polymer being a homopolymer or a copolymer of 3-acryloylaminobenzeneboronic acid, 3-methacryloylaminobenzeneboronic acid or 4-vinylbenzeneboronic acid, and a releasable amount of insulin or its derivative being 0–500 µg/ml in response to sugar concentration of 0–500 mg/dl.

3. The polymer insulin complex as claimed in claim 2, wherein the polymer having benzene boronic acid groups is a copolymer of 3-acryloylaminobenzeneboronic acid and N-vinylpyrrolidone, and said complex further comprises a polyvinyl alcohol.

4. The polymer insulin complex as claimed in claim 2, wherein the insulin is glucosylated insulin or tris (hydroxymethyl) aminomethane insulin.

5. The polymer insulin complex as claimed in claim 2, wherein the polymer is a copolymer of 3-methacryloylaminobenzeneboronic acid/2-hydroxyethyl methacrylate/ethyleneglycol dimethacrylate, 3-methacryloylaminobenzeboronic acid/2-hydroxyethyl methacrylate/diethyl-aminoethyl methacrylate, 3-methacryloylaminobenzeneboronic acid/N, N-dimethylacrylamide/ethyleneglycol dimethacrylate, 3-methacryloylaminobenzeneboronic acid/N, N-dimethylacrylamide/glycerol monomethacrylate/ethyleneglycol dimethacrylate, 3-acryloylaminobenzeneboronic acid/N, N-dimethylacrylamide/glycerol monomethacrylate/ethyleneglycol dimethacrylate, 3-methacryloylaminobenzeboronic acid/N, N-dimethylacrylamide/N, N'-methylenebisacrylamide, 3-methacryloylaminobenzeneboronic acid/N, N-dimethylacrylamide/ethyleneglycol dimethacrylate, or 3-methacryloylaminobenzeneboronic acid/acrylamide/glycerol monomethacrylate/N, N'-methylenebisacrylamide and insulin is glucosylated insulin or tris (hydroxy-methyl) aminomethane insulin.

\* \* \* \* \*